(12) United States Patent
Lejeune et al.

(10) Patent No.: US 9,198,439 B2
(45) Date of Patent: Dec. 1, 2015

(54) BREAD-MAKING WITH A HIGH YEAST CONTENT

(71) Applicant: LESAFFRE ET COMPAGNIE, Paris (FR)

(72) Inventors: Pascal Lejeune, Tourcoing (FR); Jean-Charles Bartolucci, Hellemmes (FR)

(73) Assignee: LESAFFRE ET COMPAGNIE, Paris (FR)

( * ) Notice: Subject to any disclaimer, the term of this patent is extended or adjusted under 35 U.S.C. 154(b) by 71 days.

(21) Appl. No.: 14/027,756

(22) Filed: Sep. 16, 2013

(65) Prior Publication Data

US 2014/0017355 A1 Jan. 16, 2014

Related U.S. Application Data

(63) Continuation-in-part of application No. PCT/FR2012/050545, filed on Mar. 15, 2012.

(30) Foreign Application Priority Data

Mar. 18, 2011 (FR) ...................................... 1152232

(51) Int. Cl.
   *A21D 8/04* (2006.01)
   *C12Q 1/04* (2006.01)
   *C12N 1/16* (2006.01)
   *C12N 1/18* (2006.01)
   *C12R 1/85* (2006.01)
   *C12R 1/865* (2006.01)

(52) U.S. Cl.
   CPC *A21D 8/047* (2013.01); *C12N 1/16* (2013.01); *C12N 1/18* (2013.01); *C12Q 1/04* (2013.01); *C12R 1/85* (2013.01); *C12R 1/865* (2013.01)

(58) Field of Classification Search
   CPC .................................. A21D 8/047; C12Q 1/04
   USPC ......................................... 426/19, 62; 435/34
   See application file for complete search history.

(56) References Cited

U.S. PATENT DOCUMENTS

2004/0175831 A1    9/2004   Thevelein

FOREIGN PATENT DOCUMENTS

EP          0511108 A1   4/2001
GB          2139473      11/1984

OTHER PUBLICATIONS

McKinnon C M et al, "Wine Yeast Preferment for Enhancing Bread Aroma and Flavor," Cereal Chemistry. American Association of Cereal Chemists, vol. 73. No. 1. Jan. 1, 1996 (Jan. 1, 1996). pp. 45-50.
Bell P J L et al, "Comparison of fermentative capacities of industrial baking and wild-type yeasts of the species *Saccharomyces cerevisiae* in different sugar median." Letters in Applied Microbiology, vol. 32. No. 4. Apr. 1, 2001 (Apr. 1, 2001). pp. 224-229.

*Primary Examiner* — Hamid R Badr
(74) *Attorney, Agent, or Firm* — Vedder Price P.C.; Thomas J. Kowalski; Deborah L. Lu

(57) ABSTRACT

The present invention aims to supply yeasts suitable for breadmaking using a large amount of yeast, as well as compositions that can give a bakery product containing said yeasts. The present invention also relates to a method of preparing a bakery product and a method of selecting yeast strains giving yeasts suitable for breadmaking using a large amount of yeast.

9 Claims, 1 Drawing Sheet

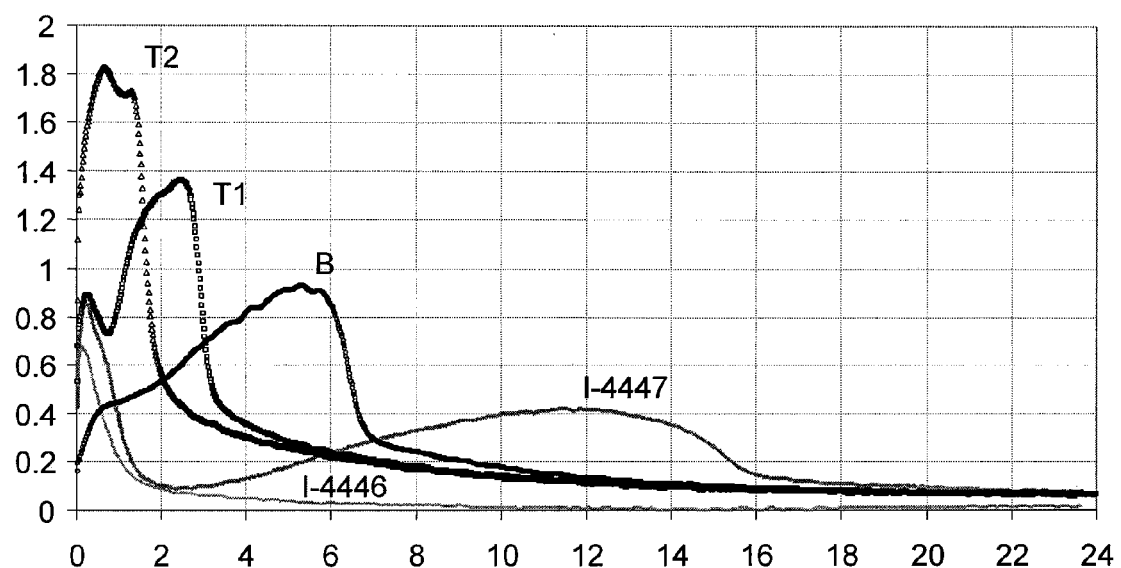

BREAD-MAKING WITH A HIGH YEAST CONTENT

CROSS-REFERENCE TO RELATED APPLICATIONS

This application is a continuation-in-part of International Patent Application No. PCT/FR2012/050545, filed Mar. 15, 2012, published as WO 2012/127156, which in turn claims priority of French application FR 11 52232, filed on Mar. 18, 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to the area of breadmaking, in particular breadmaking requiring the use of large amounts of yeast.

BACKGROUND

Yeast plays a key role in breadmaking. In particular, the fermentative activity of the yeast is reflected in release of gas, causing the dough to rise.

However, some types of breadmaking lead to a decrease in the fermentative activity of the yeast, for example owing to stresses to which the yeast is subjected, such as a high sugar content of the dough or deep-freezing of the dough before fermentation. Even using yeasts that are adapted to these stresses, it is necessary to use a larger amount of yeast in the dough.

Moreover, it may be necessary to use a larger amount of yeast to compensate for a less suitable procedure. For example, release of gas might be reduced owing to insufficient kneading and/or lack of heating power of the baking equipment. This is notably the case with domestic applications, with manual kneading, baking in a domestic oven or breadmaking in a bread machine. The release of gas may also be less because of a short breadmaking scheme, i.e. with a greatly reduced fermentation time.

In order to solve the aforementioned problems, larger amounts of yeast are therefore used. However, this has the drawback of giving bakery products that develop an undesirable aromatic note, called "yeasty note" hereinafter.

Leavens, also called preferments, are traditionally used in breadmaking for improving the organoleptic qualities of bread. Some authors have been interested in preferments obtained from nonbaking yeasts.

Thus, McKinnon et al. (Cereal Chem. 73(1): 45-50, 1996) describe liquid preferments based on oenological yeasts. However, the strains of *Saccharomyces* tested give an aroma similar to the control bakery strain and were rejected by the authors. Only strains of *Torulaspora delbrueckii* and one strain of *Hansenula anomala* give different aromas in the liquid preferment.

Although they offer certain benefits for improving the organoleptic properties of bread, the use of leavens has several drawbacks, including the time taken to produce them, their limited storage life, homogeneity of the bakery products obtained and/or the cost of the leaven if it is purchased readymade. Moreover, the use of leavens generates a typical range of aromas, namely aromatic notes of the "acid" or "vinegar" type, which are undesirable in the intended applications.

There is a real need to provide a method for obtaining the desired bakery products, but with partial or complete masking of the yeasty note, despite the presence of stresses, such as a high sugar content in the dough and/or deep-freezing of the dough, and/or despite a less suitable procedure, for example in domestic applications. Moreover, said method must not alter the habits of the consumer (professional or not), both in terms of duration of the method, number of steps and, preferably, number of ingredients to be used.

SUMMARY OF THE INVENTION

A first object of the invention relates to a method of selecting a yeast strain enabling yeasts to be obtained that are suitable for breadmaking with a high yeast content.

A second object of the invention relates to a composition that can give a bakery product, comprising yeast, flour and salt, characterized in that said yeast has a fermentative power in dry form below 70 ml in a sugar-free dough.

A third object of the invention relates to a method of preparing said composition that can give a bakery product, comprising a step of mixing the ingredients comprising yeast, flour and salt, said yeast having a fermentative power in dry form below 70 ml in a sugar-free dough.

A fourth object of the invention is a method of preparing a bakery product comprising the following steps:
  a) a step of mixing the ingredients comprising yeast, flour, salt and water, said yeast in dry form having a fermentative power below 70 ml in a sugar-free dough, to obtain a dough,
  b) a fermentation step of the dough, to obtain a fermented dough, and
  c) a step of baking the fermented dough to obtain a bakery product.

A fifth object of the invention relates to the use of a yeast whose fermentative power in dry form is below 70 ml in a sugar-free dough, as leavening agent and agent masking the yeasty note.

BRIEF DESCRIPTION OF THE DRAWINGS

FIG. 1: Fermentation profile over 24 h at 30° C. of yeasts in dry form (for dough containing 20 g of flour and 320 mg of dry yeast by weight of dry matter). The rate of gas release (in ml of $CO_2$ per minute) is shown as a function of time (in hours). T1 (curve with squares) is a baker's yeast used traditionally in sweet doughs. T2 (curve with triangles) is a baker's yeast used traditionally in sugar-free doughs. B (curve with circles) is a brewer's yeast. The rate of gas release obtained with the yeast from strain I-4446 is shown as a thin gray line and that of the yeast from strain I-4447 as a thick gray line.

DETAILED DESCRIPTION OF THE INVENTION

The inventors demonstrated, surprisingly and unexpectedly, that certain yeast strains that are not used in bakery applications give yeasts that can be used both as leavening agent and agent for masking the yeasty note in breadmaking using a high dose of yeast.

The yeasts obtained from the yeast strains according to the invention thus provide a simple solution to the problems mentioned above, by replacing traditional baker's yeast, without altering the characteristics of the bakery product and without involving other modifications of the breadmaking process, apart from optionally a larger amount of yeast used.

Thus, the habits of the consumer (whether a professional or not) are not changed in terms of duration of the method, number of steps, and number and type of ingredients to be used.

The solution provided by the yeasts according to the invention makes it possible moreover to avoid the use of leaven, preferment or starter.

Another advantage of the yeasts according to the invention is that they can be in the same format as traditional baker's yeast, for example in the form of liquid yeast, compressed yeast or dry yeast.

Therefore there is no change in the storage life of the basic ingredient, namely yeast, for the consumer.

The masking of the yeasty note can be partial or complete.

"Partial masking of the yeasty note" means a decrease of the yeasty note in the bakery product.

"Complete masking of the yeasty note" means absence of a yeasty note in the bakery product.

The term "masking" is used here in a broad sense.

The masking of the yeasty note can in fact be obtained by a decreased concentration or a disappearance, in the bakery product, of at least one aromatic molecule contributing to the yeasty note and/or by the appearance of at least one molecule that masks the yeasty note partially or completely.

A partial masking of the yeasty note is notably reflected in a decrease of the yeast aroma and/or of the yeast odor of the bakery products.

The expressions "partially mask the yeasty note" and "reduce the yeasty note" are synonyms here.

A complete masking of the yeasty note is reflected in the disappearance of the yeast aroma and yeast odor in the bakery products.

The yeast aroma and yeast odor can be evaluated by sensory analysis or by chemical measurement, as indicated below.

In the absence of stresses in the dough, in particular in the case of a sugar-free dough and in a suitable protocol, baker's yeast is used at about 0.7% of yeast, the percentage being expressed as weight of dry matter relative to the weight of flour.

A sugar-free dough denotes here a dough to which no sugar has been added.

In a sugar-free dough, the sugars present are derived from the flour.

Types of breadmaking using a high dose of yeast are defined here as breadmaking using more than 0.7% of yeast, preferably at least 0.9% of yeast, the percentages being expressed as weight of dry matter relative to the weight of flour.

The expressions "high dose of yeast" and "large amount of yeast" are synonyms here.

This difference in the amount of yeast used may seem small, but it is sufficient to impart a yeasty note to the bakery products obtained with at least 0.9% of yeast, the percentage being expressed as weight of dry matter relative to the weight of flour.

The expression "percentage expressed as weight relative to the weight of flour" is synonymous here for "baker's percentage".

The baker's percentage always refers to the weight of a given ingredient of a dough, relative to the total weight of flour in said dough.

As the yeast can be in the form of a liquid yeast, a compressed yeast or a dry yeast, the percentages of yeast are expressed as the weight of yeast dry matter relative to the weight of flour.

Surprisingly, the yeasts according to the invention permit masking of the yeasty note, even when a larger amount of yeast is used.

A larger amount of yeast is used in order to obtain an equivalent fermentative activity to traditional baker's yeast.

"Traditional baker's yeast" means here the *Saccharomyces cerevisiae* yeast usually employed in a given breadmaking.

A given breadmaking is defined here by a breadmaking recipe and protocol.

The recipe states the amount of each ingredient used.

The breadmaking protocol gives the parameters of the various steps in breadmaking.

The expression "equivalent fermentative activity" signifies that the release of gas in the dough is equivalent.

An equivalent fermentative activity is reflected in particular in a specific volume of the equivalent bakery product.

The specific volume of a bakery product is equivalent to that of a bakery product prepared with a traditional baker's yeast, if the difference between their specific volume is less than ±10%.

The specific volume of a bakery product is defined as the volume of the bakery product relative to its weight (in cm3/g).

The fermentative activity of a yeast can be evaluated by measuring its fermentative power.

The fermentative power of a yeast corresponds to the volume of CO2 (in ml) produced by the yeast in fermentation in a dough.

The expression "yeast strain" denotes a relatively homogeneous population of yeast cells.

A yeast strain is obtained starting from isolation of a clone, a clone being a population of cells obtained from a single yeast cell.

A yeast is obtained by culture of a yeast strain, i.e. by seeding an amount of a yeast strain in a culture medium, then culturing in conditions permitting multiplication of the yeast cells.

The inventors have developed an original method of selection of a yeast strain enabling yeasts to be obtained suitable for breadmaking with a high yeast content.

The present invention thus relates to a method of selecting a yeast strain giving a yeast that masks the yeasty note completely or partially, comprising the following steps:

a step of culturing a yeast strain to be tested, to obtain a yeast to be tested, a step of preparing a control bakery product starting from a dough comprising flour, salt, water and at least 0.9% of a baker's yeast, the percentage being expressed as weight of dry matter relative to the weight of flour, a step of preparing a bakery product to be tested identical to the step of preparing the control bakery product, except that the yeast is the yeast to be tested in an amount making it possible to obtain a specific volume equivalent to that of the control bakery product, a step of selecting at least one yeast that partially or completely masks the yeasty note in the bakery product to be tested in comparison with the control bakery product, and a step of selecting the yeast strain corresponding to the yeast that partially or completely masks the yeasty note in the bakery product to be tested.

The yeast strains to be tested are preferably strains of *Saccharomyces*.

The strains of *Saccharomyces* are as defined in the reference work The yeasts, a taxonomic study, by Kurtzman and Fell, 14th edition, 1998.

The strains of *Saccharomyces* comprise in particular the species cerevisiae, exigus and bayanus.

The yeast strains tested are not strains of traditional baker's yeast, and more generally are not yeast strains used as leavening agent in breadmaking.

The yeast strains tested are for example yeast strains intended for the production of alcohol, such as the so-called "potable" alcohol, intended for the manufacture of alcoholic drinks, and/or industrial alcohol, intended for example for biofuels or for the chemical industries, oenological yeast strains (also called vinification yeast strains), or collection yeast strains, which are not used in bakery, distillery, brewery or vinification applications.

The yeast tested can be in the form of a liquid yeast, a compressed yeast or a dry yeast.

The yeast tested is preferably in the form of a dry yeast.

The baker's yeast used in the method of selection for preparing the control bakery product is a traditional baker's yeast as defined above.

The yeast tested and the baker's yeast used in the control bakery product are in the same form, preferably in dry form.

The present invention also relates to a method of selection as defined above, in which the bakery product to be tested is prepared starting from a dough comprising at least 1.3% of yeast to be tested, the percentage being by weight of dry matter relative to the weight of flour.

In a preferred embodiment, the present invention relates to a method of selection as defined above, in which the bakery product to be tested is prepared starting from a dough comprising 0.9% to 3.2% of the yeast to be tested, preferably from 1.1% to 1.9% of the yeast to be tested, the percentage being by weight of dry matter relative to the weight of flour.

The dough of the bakery product to be tested therefore comprises the yeast to be tested in an amount making it possible to obtain a specific volume equal to plus or minus 10% of the specific volume of the control bakery product.

The present invention relates to a method of selection as defined above, in which the step of preparing a bakery product comprises the following substeps:
mixing the ingredients comprising flour, salt, water and yeast, to obtain a dough,
optionally deep-freezing the dough or blocking the dough at a temperature below 15° C.,
fermenting the dough, to obtain a fermented dough, and baking the fermented dough to obtain a bakery product.

Dough blocking is an intermediate step of storage of the dough at a temperature below 15° C.

The present invention also relates to a method of selection as defined above, in which the step of preparing the bakery product comprises as an ingredient at least 10% of sugar, preferably at least 15% of sugar, the percentage being expressed by weight relative to the weight of flour.

In a preferred embodiment, the present invention relates to a method of selection as defined above, in which the step of preparing the bakery product comprises as an ingredient 15% to 25% of sugar, the percentage being expressed by weight relative to the weight of flour.

The sugar is for example sucrose, glucose, fructose or a mixture thereof.

In a particular embodiment, the present invention relates to the method of selection as defined above, characterized in that at least one of the substeps of the step of preparing a bakery product is carried out in a bread machine.

In an advantageous embodiment, the present invention relates to the method of selection as defined above, characterized in that all the substeps of the step of preparing a bakery product are carried out in a bread machine.

In a particular embodiment, the present invention relates to the method of selection as defined above, characterized in that the step of preparing a bakery product is carried out according to a short scheme.

A short scheme means that the time between the start of the mixing step and the end of the baking step is less than or equal to 3 h, preferably less than or equal to 2.5 h, preferably less than or equal to 2 h.

The step of selecting at least one yeast that completely or partially masks the yeasty note in the bakery product to be tested can be carried out by any suitable means, such as sensory analysis, chemical measurement, or sensory analysis coupled to chemical measurement.

Sensory analysis consists for example of evaluating the yeasty note in the bakery product and comparing the result obtained with that of the control bakery product prepared with a traditional baker's yeast.

The evaluation of the yeasty note is preferably carried out by a panel of experts.

A panel studies, in an ordered and structured manner, the properties of a product in order to describe, classify or improve it objectively and rigorously.

The experts are qualified subjects who have good sensory acuity, are trained in the use of the methods of sensory evaluation and are capable of performing all the types of tests reliably. The experts' performance is preferably checked regularly.

The yeasty note can be evaluated by evaluating the yeast aroma and/or yeast odor.

The evaluation can be done by ascribing a score, for example on a scale from 0 to 10, depending on the intensity of the yeasty note, for example depending on the intensity of the yeast aroma and/or of the yeast odor.

The maximum intensity (score 10) ascribed to the yeast aroma or to the yeast odor corresponds respectively to the yeast aroma and yeast odor of a baguette obtained from a frozen raw dough and then baking, said baguette being prepared with 6% (by weight relative to the weight of flour) of traditional baker's yeast at 32% of dry matter (for example Hirondelle blue).

A yeast is then selected if the score ascribed to the bakery product to be tested, prepared with said yeast, for the yeasty note, i.e. for the yeast aroma and/or the yeast odor, is lower than that of the control bakery product.

Chemical measurement consists, firstly, of identifying at least one aromatic molecule corresponding to the yeasty note in the control bakery product, then comparing the amount of said aromatic molecule in the bakery product to be tested relative to the amount of said aromatic molecule in the control bakery product.

The term "identifying at least one aromatic molecule" signifies identifying said aromatic molecule structurally and/or analytically.

The aromatic molecule can for example be identified from a particular peak obtained by gas chromatography coupled to mass spectrometry or olfactometry.

The identification and evaluation of the amount of an aromatic molecule can for example be done by extraction of the aromas from the crumb of the bakery product by the so-called "Purge and trap" technique, as described in Madrera et al. (Journal of Chromatography, 2005, 245-251), then gas chromatography followed by mass spectrometry and/or olfactometry.

The amount of the aromatic molecule can be measured quantitatively or qualitatively.

For example, we can compare the intensity of the peak corresponding to the aromatic molecule in the bakery product to be tested and in the control bakery product.

In an advantageous embodiment, identification of at least one aromatic molecule corresponding to the yeasty note in the control bakery product is carried out on at least two control bakery products, preferably at least three control bakery products, prepared with increasing amounts of baker's yeast.

A yeast is then selected if the amount of said aromatic molecule measured in the bakery product to be tested prepared with said yeast is lower than that measured in the control bakery product.

In the foregoing and hereinafter, a control bakery product is obtained according to the same protocol and the same recipe as the bakery product tested, except for the yeast used and the amount thereof. In particular, the control bakery product uses a yeast in the same form as the yeast tested (for example dry, compressed or liquid form).

The present invention also relates to the yeast strains obtained by the method of selection as defined above.

The yeast strains according to the invention are not strains of traditional baker's yeast, and more generally are not yeast strains used as leavening agent in breadmaking.

The yeasts obtained by culturing the yeast strains according to the invention make it possible to mask, completely or partially, the yeasty note in the bakery products, in particular in the bakery products prepared with a high dose of yeast.

Surprisingly and unexpectedly, the inventors have demonstrated that the yeasts obtained by culturing the yeast strains according to the invention have a quite particular fermentation profile.

Thus, the yeasts according to the invention are characterized by a fermentative power, in dry form, below 70 ml in a sugar-free dough, preferably below 60 ml in a sugar-free dough.

The fermentative power is measured in a dough containing 20 g of flour for a time of 2 hours at 30° C., as defined below.

The fermentative power of the yeasts according to the invention in a sugar-free dough is well below both that of a yeast suitable for sugar-free doughs, but also well below that of a yeast suitable for sweet doughs and which therefore does not have very good performance on sugar-free dough.

Moreover, the yeasts according to the invention are characterized by a fermentative power, in dry form, below 90 ml, preferably below 80 ml in a dough with sugar at 10%.

The fermentative power of the yeasts according to the invention in a dough with sugar at 10% is well below that of a yeast suitable for sweet doughs, but also that of a yeast suitable for sugar-free doughs and which therefore does not have very good performance on sweet dough.

Finally, the yeasts according to the invention are characterized by a fermentative power, in dry form, below 70 ml in a dough with sugar at 20%, and therefore well below that of a yeast suitable for sweet doughs.

The fermentative power is measured according to classical techniques known by a person skilled in the art, adapted from the protocol described by Burrows and Harrison in "Journal of the Institute of Brewing", Vol 65, 1959.

The fermentative power is notably measured using a fermentometer or a Risograph® (National Manufacturing, Lincoln, Nebr.).

The fermentative power is measured here on a dough consisting of flour and a dry yeast, for a time of 2 hours (cf. example 1).

The fermentative power is measured in a sugar-free dough and in doughs with sugar at 10% and 20% (percentages expressed by weight relative to the weight of flour).

The fermentative power of a yeast in a sugar-free dough is measured here in a dough containing 20 g of flour.

The fermentative power of a yeast in a dough with sugar at 10% or 20% is measured here in a dough containing 20 g of flour and 2 g or 4 g of sucrose respectively.

The dry yeast, in an amount equal to 160 mg of dry matter, is rehydrated, then suspended in an aqueous solution containing 27 g/l of NaCl (cf. example 1).

The flour (with or without sucrose) and said yeast suspension are then mixed for 40 seconds in a kneader, so as to obtain a dough which is then put in a vessel on a water bath at 30° C. 13 minutes after the start of mixing, the vessel containing the dough is closed hermetically.

The volume of gas released is measured during the 1st hour and during the 2nd hour, by means of a Risograph® (National Manufacturing, Lincoln, Nebr.). Then the total volume in ml over 2 hours at 30° C. is stated.

Finally, surprisingly, the inventors showed that the yeasts according to the invention make it possible not only to mask the yeasty note completely or partially, but also to supply a positive note that is absent from the control bakery product and which differs depending on the type of breadmaking.

The method of selection according to the invention thus made it possible to select the following three yeast strains: the strain deposited at the CNCM under number I-4445, the strain deposited at the CNCM under number I-4446 and the strain deposited at the CNCM under number I-4447.

The yeast strains I-4445, I-4446 and I-4447 were deposited on the basis of the Budapest Treaty on Feb. 9, 2011 at the CNCM (Collection Nationale de Cultures de Microorganismes), 25 rue du Docteur Roux, 75724 Paris cedex 15, France.

The yeast strain I-4445 is a distillery strain, usually employed for alcohol production.

The yeast strain I-4445 is a strain of *Saccharomyces cerevisiae*.

The yeast obtained by cultivation of yeast strain I-4445 has a fermentative power, in dry form, below 60 ml in a sugar-free dough, below 70 ml in a dough with sugar at 10% and below 50 ml in a dough with sugar at 20% (cf. example 1).

The yeast obtained by cultivation of yeast strain I-4445 makes it possible to reduce the yeasty note of bakery products containing large amounts of yeast, in particular in breadmaking in a bread machine, in sweet doughs, in frozen raw doughs and/or in breadmaking according to a short scheme (cf. example 2).

The yeast obtained by cultivation of yeast strain I-4445 can also supply a positive note in several types of breadmaking (cf. example 2), such as:
  an almond odor and aroma, for example in a brioche-type bread made in a bread machine,
  a ripe wheat odor and aroma, for example in sugar-free doughs, such as a baguette obtained in a direct scheme,
  a rum odor and aroma, for example in a brioche obtained from a frozen raw dough or a rotimani, and
  a sweet flavor, for example in very sweet doughs, such as that of rotimani.

Rotimani is an Indonesian sandwich bread obtained from a dough with a very high sugar content.

The yeast strain I-4446 is a yeast strain in the applicant's collection, which is not used in distillery, oenology, brewery, or bakery as leavening agent.

The yeast strain I-4446 is a strain of *Saccharomyces cerevisiae*.

The yeast obtained by cultivation of yeast strain I-4446 has a fermentative power, in dry form, below 45 ml in a sugar-free dough, below 80 ml in a dough with sugar at 10% and below 65 ml in a dough with sugar at 20% (cf. example 1).

The yeast obtained by cultivation of yeast strain I-4446 makes it possible to reduce the yeasty note of bakery products containing large amounts of yeast, in particular in breadmaking in a bread machine, in sweet doughs, in frozen raw doughs and/or in breadmaking according to a short scheme (cf. example 2).

The yeast obtained by cultivation of yeast strain I-4446 can also supply a positive note in several types of breadmaking (cf. example 2), such as:
- a rum odor and aroma, for example in sweet doughs, such as in a brioche-type bread made in a bread machine, in a brioche obtained from a frozen raw dough or a rotimani, and
- a sweet flavor, for example in very sweet doughs, such as that of rotimani.

The yeast strain I-4447 is an oenology strain, usually employed in vinification.

The yeast strain I-4447 is a strain of *Saccharomyces bayanus*.

The yeast obtained by cultivation of yeast strain I-4447 has a fermentative power, in dry form, below 55 ml in a sugar-free dough, below 80 ml in a dough with sugar at 10% and below 70 ml in a dough with sugar at 20% (cf. example 1).

The yeast obtained by cultivation of yeast strain I-4447 makes it possible to reduce the yeasty note of bakery products containing large amounts of yeast, in particular in breadmaking in a bread machine, in sweet doughs, in frozen raw doughs and/or in breadmaking according to a short scheme (cf. example 2).

The yeast obtained by cultivation of yeast strain I-4447 can also supply a positive note in several types of breadmaking (cf. example 2), such as:
- an almond odor and aroma, for example in a brioche-type bread made in a bread machine,
- a ripe wheat odor and aroma, for example in a sugar-free dough such as a baguette obtained in a direct scheme,
- a sweet flavor and/or an aroma of rum, for example in very sweet doughs, such as that of rotimani.

The present invention also relates to all the strains derived from the yeast strains according to the invention and which share the same properties of complete or partial masking of the yeasty note.

The present invention relates more particularly to strains derived from the yeast strains according to the invention, said derived strains giving yeasts having a fermentative power below 70 ml, in dry form, in a sugar-free dough.

The fermentative power is as measured above.

The expression "derived strain" denotes a strain derived by any transformation whatever, for example one or more crossings and/or one or more mutations and/or one or more genetic transformations.

A strain derived by crossing can be obtained by crossing a strain according to the invention with the same strain, or another strain according to the invention, or any other strain.

A strain derived by mutation can be a strain that has undergone at least one spontaneous mutation in its genome or at least one mutation that has been induced, for example by mutagenesis.

The mutation or mutations of the derived strain may be silent or not.

The expression "mutagenesis" denotes both classical mutagenesis obtained by radiation or by mutagenic chemicals, and insertion mutagenesis by transposition or by integration of an exogenous DNA fragment.

Irradiation mutagenesis comprises the use of UV, X, or gamma radiation.

Mutagenic chemicals are for example EMS (ethyl-methyl sulfonate), EES (ethyl-ethyl sulfonate), nitrosoguanidine, nitrous acid, aflatoxin B1, hydroxylamine, 5-bromouracil, 2-aminopurine, proflavin and/or acridine orange. A strain derived by genetic transformation is a strain into which exogenous DNA has been introduced.

Said exogenous DNA can be supplied by a plasmid.

Said exogenous DNA is preferably integrated in the yeast genome.

The invention also relates to a method of transformation of a yeast strain according to the invention, to obtain a derived strain as defined above, said method of transformation comprising a step of transformation of said strain by at least one crossing and/or at least one mutation and/or at least one genetic transformation.

The present invention also relates to the yeast strains obtainable by the method of transformation as defined above.

The present invention also relates to a yeast obtained by culture of a yeast strain as defined above or by culture of a derived yeast strain as defined above.

A yeast according to the invention is obtained by culture of a yeast strain according to the invention, notably as described in the reference work "Yeast Technology", 2nd edition, 1991, G. Reed and T. W. Nagodawithana, published by Van Nostrand Reinhold, ISBN 0-442-31892-8.

Obtaining a yeast according to the invention on an industrial scale generally comprises at least the first two steps of the following set of steps:
- multiplication of a yeast strain in a culture medium in several stages, firstly in semi-anaerobiosis, then in aerobiosis,
- separation of the yeast thus produced from its culture medium by centrifugation, to obtain a liquid yeast cream containing between about 12 and 25% of dry matter, or an even higher content of dry matter if the yeast cream is mixed with osmolytes,
- filtration of the liquid yeast cream thus obtained, generally on a rotary filter under vacuum, to obtain a dehydrated fresh yeast containing 26% to 35% of dry matter,
- mixing of said dehydrated fresh yeast, to obtain a homogeneous paste, extrusion of the yeast thus obtained, to obtain:
  - a compressed yeast in the form of blocks of fresh yeast or crumbled fresh yeast, containing about 30% of dry matter, or
  - a yeast in the form of particles, generally granules, if the yeast is intended to be dried,
- optionally, controlled drying, in a hot air stream, for example by fluidization, of the yeast particles obtained by extrusion to obtain dry yeast.

The drying step is preferably gentle rapid drying in the presence of an emulsifier.

Among the emulsifiers that can be used in the drying step, sorbitan monostearate can be selected, used for example at a concentration of about 1.0% (by weight relative to the weight of dry yeast).

The yeasts according to the invention can be used in any possible form.

For example, the present invention relates to a yeast as defined above, characterized in that it is in the form of yeast cream, compressed yeast, dry yeast or frozen yeast.

Fresh yeasts are characterized by a higher water content compared to dry yeasts. Fresh yeasts include yeast creams and compressed yeasts.

Yeast creams, also called "liquid yeasts", are aqueous suspensions of yeast cells with a viscosity of the cream type.

Yeast cream means a liquid suspension, typically an aqueous suspension, of live yeast cells, said suspension having a content of dry matter of at least 12 wt %, generally from about 12 to about 50 wt % (extended definition of yeast cream).

Preferably, the yeast cream conforms to the definition in the strict sense, i.e. it has a dry matter content from about 12 to about 25 wt %, preferably from about 14 to about 22 wt %.

Among the compressed yeasts, a distinction is made between compressed yeasts in compact blocks, also called "yeast cakes", which are characterized by a dry matter content from about 26% to about 35%, and compressed yeasts in granules, which are characterized by a water content from about 21% to about 35%.

Dry yeasts are characterized by a dry matter content above about 92%.

Frozen yeasts are characterized by a dry matter content from about 74% to about 80%.

The present invention also relates to a composition that can give a bakery product, comprising a yeast according to the invention, flour and salt.

The yeast according to the invention is a yeast as defined above.

In particular, the yeast according to the invention makes it possible to mask, partially or completely, the yeasty note of bakery products that use a high dose of yeast.

A yeast according to the invention is called, for simplicity, as follows: "yeast masking the yeasty note completely or partially".

A preferred yeast according to the invention makes it possible not only to mask the yeasty note completely or partially, but also to supply a positive note that is absent in the bakery product obtained with a traditional baker's yeast.

The present invention relates more particularly to a composition that can give a bakery product, comprising a yeast, flour and salt, characterized in that said yeast is obtained by culture of a yeast strain according to the invention.

A yeast strain according to the invention is a yeast strain as defined above.

The expression "that can give a bakery product" signifies that, optionally apart from water, the composition contains the essential ingredients for obtaining a dough.

In particular, the expression "that can give a bakery product" excludes the bakery composition according to the invention being a leaven or a starter.

A leaven, also called preferment, is a product generating or containing one or more organic acids and obtained by fermentation of a substrate by means of a biomass, said substrate predominantly containing flour, said biomass containing at least one bacterium.

The bacterium or bacteria can come from the flour.

The bacterium or bacteria are preferably lactic-acid bacteria.

A leaven can be a dry leaven, a pasty leaven or a liquid leaven.

The leaven can be obtained from a starter.

A starter is a composition, generally in the form of concentrate or of cream, containing one or more species of lactic-acid bacteria.

The dry leavens are also called fermented flour, dehydrated fermented flour, prefermented flour, and dehydrated leaven.

A composition according to the invention can comprise a leaven and/or a starter, in addition to a yeast according to the invention, flour and salt.

However, in a preferred embodiment, the composition according to the invention comprises neither leaven nor starter, and more generally no preparation obtained after a phase of fermentation.

A bakery product according to the invention is, preferably, a bakery product obtained by oven baking of a dough fermented by a yeast.

A bakery product according to the invention is for example selected from bread, brioche, sandwich bread, and pastries made with sweetened dough.

The oven can be any type of oven, including a bread machine.

In a preferred embodiment, the oven is not a microwave oven.

In an advantageous embodiment, the bakery product according to the invention is not a bakery product obtained by cooking a fermented dough with steam or by frying, for example to obtain a donut.

In another advantageous embodiment, the bakery product according to the invention does not comprise tarts, pizzas, cakes, or biscuits.

The present invention relates more particularly to a composition that can give a bakery product, comprising a yeast, flour, and salt, characterized in that said yeast has a fermentative power in dry form below 70 ml in a sugar-free dough, preferably below 60 ml in a sugar-free dough.

The fermentative power is measured in a dough containing 20 g of flour for a time of 2 hours at 30° C., as defined above.

The present invention also relates to a composition that can give a bakery product, as defined above, characterized in that said yeast in dry form has a fermentative power below 90 ml in a dough with sugar at 10%, preferably below 80 ml in a dough with sugar at 10%.

The present invention also relates to a composition that can give a bakery product, as defined above, characterized in that said yeast in dry form has a fermentative power below 70 ml in a dough with sugar at 20%.

A preferred composition according to the invention is thus a composition as defined above, characterized in that said yeast in dry form has a fermentative power:

below 70 ml in a sugar-free dough, preferably below 60 ml in a sugar-free dough,
below 90 ml in a dough with sugar at 10%, preferably below 80 ml in a dough with sugar at 10%, and
is below 70 ml in a dough with sugar at 20%.

The yeast is characterized here by a fermentative power measured on dry yeast.

However, in the composition according to the invention, the yeast can be used in any form, for example a liquid yeast, a compressed yeast or a dry yeast.

Liquid yeast, compressed yeast and dry yeast are as defined above.

As already mentioned, the present invention makes it possible to completely replace the traditional baker's yeast with a single yeast, which is used both as leavening agent and agent for masking the yeasty note.

The yeast according to the invention can therefore completely replace the traditional baker's yeast and it is not necessary to add a traditional baker's yeast to supplement the yeast according to the invention.

A preferred composition according to the invention does not comprise traditional baker's yeast, and more generally does not comprise yeast usually employed in breadmaking.

Thus, a preferred composition according to the invention is a composition that can give a bakery product, comprising a yeast, flour, and salt, characterized in that said yeast has a fermentative power in dry form below 70 ml in a sugar-free dough and in that said yeast constitutes the leavening agent.

The expression "said yeast constitutes the leavening agent" signifies that said yeast is the only source of leavening agent in the composition.

A preferred yeast according to the invention is a yeast as defined above which is also capable of producing, at 35° C., at least 13° of Gay-Lussac alcohol, preferably at least 13.5°, in a synthetic medium comprising sugar in a nonlimiting amount, a source of nitrogen, a source of phosphorus, as well as the vitamins and minerals essential to the growth of a yeast.

Such a yeast is for example a yeast obtained by cultivation of yeast strain I-4445.

A synthetic medium of this kind comprises for example 265 g/kg of glucose, 2.47 g/kg of ammonium acetate, 0.72 g/kg of potassium dihydrogen phosphate, 0.3 g/kg of ammonia, 5 g/kg of yeast extract, 10 mg/kg of inositol, 4 mg/kg of vitamin B1, 4 mg/kg of vitamin B6, 40 mg/kg of nicotinic acid, 0.004 mg/kg of biotin, the pH being adjusted to 5.5.

Another preferred yeast according to the invention is a yeast as defined above, whose fermentation profile over 24 h of fermentation at 30° C. in a sugar-free dough obtained according to the protocol for measurement of the fermentative power, but with 320 mg of yeast dry matter, has all of the following characteristics:

a first peak of the rate of gas release during the first hour of fermentation,
a rate of gas release at 2 hours below 0.30 ml/min,
a cumulative gas release at 2 hours below 90 ml, and
a second peak of the rate of gas release in a time of more than 8 hours or no second peak.

This is notably the case with the yeast obtained by cultivation of yeast strain I-4446 or yeast strain I-4447 (cf. FIG. 1).

Brewer's yeasts and traditional baker's yeasts have a completely different fermentation profile (cf. FIG. 1).

The present invention relates to a composition as defined above, characterized in that it comprises at least 0.9% of said yeast, the percentage being expressed as weight of dry matter relative to the weight of flour.

The present invention relates in particular to a composition as defined above, characterized in that it comprises flour, salt, and at least 0.9% of said yeast masking the yeasty note completely or partially, said yeast having a fermentative power in dry form below 70 ml in a sugar-free dough.

The fermentative power is measured as defined above.

The present invention also relates to a composition as defined above, characterized in that it comprises for example at least 1.3% of said yeast, the percentage being expressed as weight of dry matter relative to the weight of flour.

A preferred composition according to the invention is a composition as defined above, characterized in that it comprises 0.9% to 3.2% of said yeast, preferably from 1.1% to 1.9% of said yeast, the percentage being expressed as weight of dry matter relative to the weight of flour.

The composition according to the invention can comprise at least two different yeasts obtained from different yeast strains according to the invention.

However, a preferred composition according to the invention comprises a single variety of yeast obtained from a yeast strain according to the invention.

The present invention relates more particularly to a composition as defined above, characterized in that said yeast is obtained by culture of a yeast strain obtained by the method of selection as defined above or a strain derived from a yeast strain obtained by said method of selection.

The present invention relates even more particularly to a composition as defined above, characterized in that said yeast is obtained by cultivation of yeast strain I-4445, yeast strain I-4446, yeast strain I-4447 or a strain derived from said yeast strains.

The present invention relates more particularly to a composition as defined above, characterized in that said yeast is obtained by cultivation of yeast strain I-4445, yeast strain I-4446, yeast strain I-4447, another yeast strain obtained by the method of selection as defined above or a strain derived from said yeast strains.

A yeast strain obtained by the method of selection as defined above and used in the composition above is not a strain of traditional baker's yeast, and more generally is not a yeast strain used in breadmaking.

The present invention also relates to a composition as defined above, characterized in that it comprises less than 90% of water, preferably less than 80% of water, more preferably less than 70% of water, the percentage being expressed by weight relative to the weight of flour.

When the composition according to the invention comprises water, the various ingredients are preferably mixed in order to obtain a homogeneous composition.

The composition according to the invention is then a dough.

The present invention thus relates in particular to a composition as defined above, characterized in that it is in the form of an unfermented dough, a fermented dough, a frozen raw dough, a frozen fermented dough, a precooked dough or a frozen precooked dough.

An unfermented dough is a dough obtained by mixing the ingredients, and more precisely by kneading.

A fermented dough is a dough obtained after the fermentation step called "final fermentation" or "final proving".

A frozen raw dough denotes herein a dough that is frozen before the final fermentation step, but after the initial fermentation step.

A precooked dough is a partially cooked fermented dough.

A frozen precooked dough is a fermented dough that is partially cooked before being frozen.

The present invention relates to a composition as defined above, characterized in that it is in dry form.

The expression "in dry form" signifies that the composition comprises at least 85% of dry matter, preferably at least 90% of dry matter, more preferably at least 95% of dry matter, the percentage being expressed by weight relative to the weight of the composition.

A composition according to the invention in dry form is preferably a preparation that is ready to use.

A preparation that is ready to use is a composition that comprises all the ingredients of the bakery product, except water and optionally another liquid such as milk.

The present invention also relates to a composition as defined above, characterized in that it comprises sugar, preferably at least 5% of sugar, more preferably at least 10% of sugar, the percentage being expressed by weight relative to the weight of flour.

A composition according to the invention can comprise at least 20% of sugar, the percentage being expressed by weight relative to the weight of flour.

The sugar is supplied for example in the form of sucrose, glucose, fructose, or a mixture thereof.

The present invention also relates to a composition as defined above characterized in that it comprises fats, milk, eggs, and/or an improver.

The milk is for example milk in powder form or in liquid form.

The fats are for example margarine, oil, butter, a derivative thereof and/or a mixture thereof.

The present invention relates for example to a composition as defined above characterized in that it comprises at least 5% of fats, preferably at least 10% of fats, even more preferably at least 15% of fats, the percentage being expressed by weight relative to the weight of flour.

An improver contains for example at least one oxidant and/or at least one reducing agent and/or at least one enzyme and/or at least one emulsifier.

Preferred compositions according to the invention are shown in Tables 2, 3, 5 or 7 of example 2, as well as these same compositions without the ingredient water.

The present invention also relates to a method of preparing a composition that can give a bakery product as defined above, comprising a step of mixing the ingredients comprising a yeast, flour and salt, said yeast having a fermentative power in dry form below 70 ml in a sugar-free dough.

Said yeast according to the invention is as defined above, obtained by culture of a yeast strain according to the invention.

The yeast strain is a yeast strain as defined above.

The fermentative power is measured in a dough containing 20 g of flour for a time of 2 hours at 30° C., as defined above.

The present invention relates in particular to a method of preparing a composition that can give a bakery product as defined above, comprising a step of mixing the ingredients comprising flour, salt and at least 0.9% of a yeast that masks the yeasty note completely or partially, the percentage being expressed as weight of dry matter relative to the weight of flour, said yeast having a fermentative power in dry form below 70 ml in a sugar-free dough.

More generally, the ingredients are as defined above, in the quantities as defined above and can comprise other ingredients as defined above.

The mixing step corresponds to the kneading step when the composition that can give a bakery product is a dough.

The present invention also relates to a method of preparing a bakery product comprising the following steps:
  a) a step of mixing the ingredients comprising a yeast according to the invention, flour, salt and water, to obtain a dough,
  b) a step of fermentation of the dough, to obtain a fermented dough, and
  c) a step of baking the fermented dough, to obtain a bakery product.

The yeast according to the invention is as defined above.

The present invention relates more particularly to a method of preparing a bakery product comprising the following steps:
  a) a step of mixing the ingredients comprising a yeast, flour, salt and water, said yeast being obtained by culture of a yeast strain according to the invention, to obtain a dough,
  b) a step of fermentation of the dough, to obtain a fermented dough, and
  c) a step of baking the fermented dough to obtain a bakery product.

A yeast strain according to the invention is as defined above.

The present invention relates in particular to a method of preparing a bakery product comprising the following steps:
  a) a step of mixing the ingredients comprising a yeast, flour, salt and water, said yeast having a fermentative power in dry form below 70 ml in a sugar-free dough, to obtain a dough,
  b) a step of fermentation of the dough, to obtain a fermented dough, and
  c) a step of baking the fermented dough to obtain a bakery product.

The fermentative power is measured as defined above.

The present invention relates in particular to a method of preparing a bakery product comprising the following steps:
  a) a step of mixing the ingredients comprising flour, salt, water and at least 0.9% of a yeast that masks the yeasty note completely or partially, the percentage being expressed as weight of dry matter relative to the weight of flour, said yeast having a fermentative power in dry form below 70 ml in a sugar-free dough, to obtain a dough,
  b) a step of fermentation of the dough, to obtain a fermented dough, and
  c) a step of baking the fermented dough to obtain a bakery product.

The mixing step a) corresponds to the kneading of the dough.

The mixing step a) can be carried out manually, in a kneader or in a bread machine.

The dough obtained at the end of step a) and the fermented dough obtained at the end of step b) preferably have the characteristics of a composition that can give a bakery product as defined above.

The mixing step a) can consist of supplying a composition that can give a bakery product as defined above.

The mixing step a) can consist of mixing a composition that can give a bakery product as defined above with water.

The steps of mixing a) and of fermentation b) can consist of supplying a composition that can give a bakery product as defined above.

In a preferred embodiment according to the invention, the ingredients mixed during step a) do not comprise a leaven and/or a starter and/or a preparation obtained after a phase of fermentation.

The present invention relates to the method of preparing a bakery product as defined above, characterized in that the ingredients comprise at least 0.9% of said yeast, preferably at least 1.3% of said yeast, the percentage being expressed as weight of dry matter relative to the weight of flour.

The present invention also relates to the method of preparing a bakery product as defined above, characterized in that the ingredients comprise 0.9% to 3.2% of said yeast, preferably from 1.1% to 1.9% of said yeast, the percentage being expressed as weight of dry matter relative to the weight of flour.

The present invention relates more particularly to the method of preparing a bakery product as defined above, characterized in that the yeast is obtained by culture of a yeast strain obtained by the method of selection as defined above or a strain derived from a yeast strain obtained by said method of selection.

The present invention relates even more particularly to the method of preparing a bakery product as defined above, characterized in that said yeast is obtained by cultivation of yeast strain I-4445, yeast strain I-4446, yeast strain I-4447 or a strain derived from said yeast strains.

The present invention relates more particularly to the method of preparing a bakery product as defined above, characterized in that the yeast is obtained by cultivation of yeast strain I-4445, yeast strain I-4446, yeast strain I-4447, another yeast strain obtained by the method as defined above or a strain derived from said yeast strains.

The present invention relates more particularly to the method of preparing a bakery product as defined above, characterized in that the ingredients in mixing step a) also comprise at least 5% of sugar, preferably at least 10% of sugar, the percentage being expressed by weight relative to the weight of flour.

Step b) of fermentation corresponds to final proving.

Step b) of fermentation is generally preceded by a 1st fermentation step called initial fermentation.

Step b) of fermentation is therefore called either 2nd fermentation or final fermentation.

The present invention also relates to a method of preparing a bakery product as defined above, characterized in that it comprises a step of deep-freezing the dough obtained in step a) before the fermentation step b).

The deep-freezing step is preferably carried out after an initial fermentation step.

The present invention also relates to the method as defined above in which the baking step is carried out in an oven or in a bread machine.

The baking step c) preferably is not carried out by cooking with steam, by microwave and/or by frying.

The present invention relates in particular to a method of preparing a bakery product as defined above, characterized in that at least one of the steps of the method is carried out in a bread machine.

The present invention also relates to a method of preparing a bakery product as defined above, characterized in that it comprises a step of precooking and/or of deep-freezing between fermentation step b) and baking step c).

The present invention relates in particular to a method of preparing a bakery product as defined above comprising the following steps:
  a step of mixing the ingredients comprising a yeast, flour, salt and water, said yeast having a fermentative power in dry form below 70 ml in a sugar-free dough, to obtain a dough,
  an initial fermentation step,
  an optional step of deep-freezing,
  a step of fermentation of the dough, to obtain a fermented dough,
  an optional step of precooking,
  an optional step of deep-freezing, and
  a step of baking the fermented dough to obtain a bakery product.

The present invention relates more particularly to a method of preparing a bakery product as defined above comprising the following steps:
  a step of mixing the ingredients comprising flour, salt, water, and at least 0.9% of a yeast that masks the yeasty note completely or partially, the percentage being expressed as weight of dry matter relative to the weight of flour, said yeast having a fermentative power in dry form below 70 ml in a sugar-free dough, to obtain a dough,
  an initial fermentation step,
  an optional step of deep-freezing,
  a step of fermentation of the dough, to obtain a fermented dough,
  an optional step of precooking,
  an optional step of deep-freezing, and
  a step of baking the fermented dough to obtain a bakery product.

The present invention also relates to the use of a yeast strain for obtaining a leavening agent and agent masking the yeasty note, characterized in that said yeast strain is selected from yeast strain I-4445, yeast strain I-4446, yeast strain I-4447, a yeast strain obtained by the method of selection as defined above or a strain derived from said yeast strains.

The yeasty note is masked partially or completely.

The present invention relates more particularly to the use as defined above of a yeast strain for obtaining a leavening agent and agent masking the yeasty note intended for breadmaking using a large amount of yeast.

The present invention relates more particularly to the use as defined above of a yeast strain for obtaining a leavening agent and agent masking the yeasty note intended for breadmaking using at least 0.9% of yeast, preferably 1.3% of yeast, by weight of dry matter relative to the weight of flour.

The present invention relates more particularly to the use as defined above of a yeast strain for obtaining a leavening agent and agent masking the yeasty note intended for breadmaking using 0.9% to 3.2% of yeast, preferably from 1.1% to 1.9% of yeast, by weight of dry matter relative to the weight of flour.

The present invention relates more particularly to the use as defined above of a yeast strain for obtaining a leavening agent and agent masking the yeasty note intended for breadmaking using at least 5% of sugar, preferably at least 10% of sugar, by weight relative to the weight of flour.

The present invention relates more particularly to the use as defined above of a yeast strain for obtaining a leavening agent and agent masking the yeasty note intended for domestic applications.

The present invention relates more particularly to the use as defined above of a yeast strain for obtaining a leavening agent and agent masking the yeasty note intended for breadmaking with frozen raw dough.

The present invention also relates to the use of a yeast whose fermentative power in dry form in a sugar-free dough is below 70 ml, as leavening agent and agent masking the yeasty note.

The fermentative power is measured as defined above.

The yeasty note is masked partially or completely.

The present invention relates in particular to the use of a yeast whose fermentative power in dry form in a sugar-free dough is below 70 ml, as leavening agent and agent masking the yeasty note in a composition that can give a bakery product.

The present invention relates more particularly to the use as defined above of a yeast, characterized in that the yeast is obtained by culture of a yeast strain obtained by the method of selection as defined above or a strain derived from a yeast strain obtained by said method of selection.

The present invention relates even more particularly to the use as defined above of a yeast, characterized in that said yeast is obtained by cultivation of yeast strain I-4445, yeast strain I-4446, yeast strain I-4447 or a strain derived from said yeast strains.

The present invention relates more particularly to the use as defined above of a yeast, characterized in that the yeast is obtained by cultivation of yeast strain I-4445, yeast strain I-4446, yeast strain I-4447, some other yeast strain obtained by the method of selection as defined above or a strain derived from said yeast strains.

The present invention relates more particularly to the use as defined above of a yeast as leavening agent and agent masking the yeasty note intended for breadmaking using a large amount of yeast.

The present invention relates more particularly to the use as defined above of a yeast as leavening agent and agent masking the yeasty note intended for breadmaking using at least 0.9% of yeast, by weight of dry matter relative to the weight of flour.

The present invention relates more particularly to the use as defined above of a yeast for obtaining a leavening agent and agent masking the yeasty note intended for breadmaking using 0.9% to 3.2% of yeast, preferably from 1.1% to 1.9% of yeast, the percentage being expressed as weight of dry matter relative to the weight of flour.

The present invention relates more particularly to the use as defined above of a yeast as leavening agent and agent masking the yeasty note intended for breadmaking using at least 5% of sugar, preferably at least 10% of sugar, the percentage being expressed by weight relative to the weight of flour.

The present invention relates more particularly to the use as defined above of a yeast as leavening agent and agent masking the yeasty note intended for domestic applications.

The present invention relates more particularly to the use as defined above of a yeast as leavening agent and agent masking the yeasty note intended for breadmaking with frozen raw dough.

The following examples illustrate but do not limit the invention.

The examples describe in particular the fermentative power of the yeasts according to the invention and the masking of the yeasty note obtained owing to the yeasts according to the invention in various breadmaking recipes and protocols.

EXAMPLES

Example 1

Characterization of the Fermentative Power of the Yeasts According to the Invention Materials and Methods (i) Production of Dry Yeasts In all the following recipes, the yeasts are used in the form of dry yeasts.

The yeasts are produced starting from the yeast strains according to the invention in fermenters, as described in the reference work "Yeast Technology", 2nd edition, 1991, G. Reed and T. W. Nagodawithana, published by Van Nostrand Reinhold, ISBN 0-442-31892-8. The yeasts are then dried to obtain dry yeasts.

(ii) Measurement of the Fermentative Power

The fermentative power of the yeasts is measured on dry yeast, in a sugar-free dough and in doughs with sugar at 10% and 20% (percentages expressed by weight relative to the weight of flour).

The dough contains 20 g of flour, to which 2 g of sucrose is added for dough with sugar at 10% and 4 g of sucrose for dough with sugar at 20%.

The dry yeast, in an amount equal to 160 mg of dry matter, is rehydrated in 6 ml of distilled water at 38° C. for 15 minutes. Then 9 ml of a mixture of water and 405 mg of NaCl is added. We thus obtain a suspension of yeast in an aqueous solution containing 27 g/l of NaCl.

The flour (with or without sucrose) and said yeast suspension are mixed for 40 seconds in a kneader, so as to obtain a dough, which is then put in a vessel on a water bath at 30° C. 13 minutes after the start of mixing, the vessel containing the dough is closed hermetically.

The volume of gas released is measured during the 1st hour and during the 2nd hour, by means of a Risograph (National Manufacturing, Lincoln, Nebr.). Then the total volume in ml over 2 hours at 30° C. is indicated.

Results

The fermentative power of the yeasts according to the invention is shown in Table 1 (gas released in ml).

The fermentative power obtained with two control yeasts is shown for comparison. T1 is a yeast suitable for use in sweet doughs and T2 in sugar-free doughs.

TABLE 1

| Yeast strain | Sugar-free dough | Sweet dough 10% | Sweet dough 20% |
| --- | --- | --- | --- |
| I-4445 | 50 | 60 | 41 |
| I-4446 | 35 | 72 | 55 |
| I-4447 | 44 | 73 | 62 |
| T1 | 76 | 101 | 115 |
| T2 | 112 | 94 | 67 |

The yeasts according to the invention have a quite particular fermentation profile: in a sugar-free dough, their fermentative power is below 60 ml, i.e. well below both that of a yeast suitable for sugar-free doughs, and that of a yeast that is suitable for sweet doughs and which therefore does not have very good performance with sugar-free dough.

The fermentative power of the yeasts according to the invention in a dough with sugar at 10% is below 80 ml, i.e. below that of a yeast suitable for sweet doughs, but also below that of a yeast that is suitable for sugar-free doughs and which therefore does not have very good performance with sugar-free dough.

Finally, in a dough with sugar at 20%, the fermentative power of the yeasts according to the invention is below 70 ml, or else below that of a yeast suitable for sweet doughs. However, the difference between the fermentative power of the yeasts according to the invention and that of a yeast suitable for a sugar-free dough is smaller in a dough with sugar at 20%.

Example 2

Decrease of the Yeasty Note Obtained Owing to the Yeasts According to the Invention in Various Breadmaking Recipes and Protocols Materials and Methods (i) Yeasts The yeasts tested are in the form of dry yeast.

(ii) Brioche-Type Bread Obtained in a Bread Machine

The recipe of the brioche-type bread (cf. Table 2) is a recipe containing 15.2% of sugar (percentage expressed relative to the weight of flour). It is applied in a bread machine (reference: Moulinex Homebread).

The "brioche" program is used with the following parameters:

weight of the bread: 750 g, baking intensity: 1.

The following are put in the pan of the bread machine:

a) water, b) salt, sugar, milk powder, margarine, c) flour, and d) yeast.

The program is started by pressing the "start" button.

At the end of the program, the brioche-type bread is taken out of the bread machine, and is then cooled on a grille.

The brioche-type bread, unsliced, is packed in a plastic bag.

The control yeast (Bruggeman brown) is a baker's yeast used conventionally for this type of breadmaking.

TABLE 2

| Ingredients | Quantity in grams | Quantity as % of the baker |
|---|---|---|
| Flour | 500 | 100 |
| Water | 270 | 54 |
| Sugar | 76 | 15.2 |
| Milk powder | 24 | 4.8 |
| Salt | 8 | 1.6 |
| Margarine | 75 | 15 |
| Dry yeast | 7.5 (5 for the control) | 1.5 (1 for the control) |

(iii) Direct-Scheme Baguette

The direct-scheme baguette is a baguette obtained according to a very short scheme, in just 2 h.

The recipe is shown in Table 3 and the protocol applied is given in Table 4.

The control yeast (Bruggeman blue) is a baker's yeast used conventionally for this type of breadmaking.

The improver supplies the mixture of oxidants and reducing agents, the enzymes as well as the conventional emulsifiers permitting optimization of the production process, good quality and good storage of the breads obtained.

TABLE 3

| Ingredients | Quantity in grams | Quantity as % of the baker |
|---|---|---|
| Flour | 1500 | 100 |
| Water | 990 | 66 |
| Salt | 27 | 1.8 |
| Dry yeast | 27 (19.5 for the control) | 1.8 (1.3 for the control) |
| Improver (Ibis blue) | 7.5 | 0.5 |

TABLE 4

| Kneader | spiral |
|---|---|
| Kneading 1st speed | 4 min |
| Kneading 2nd speed | 3 min + 1 min |
| Initial fermentation (1st fermentation) | 30 min |
| Division | 330 g |
| Balling | |
| Relaxation | 10 min |
| Working | Somewhat tight |
| Final proving (2nd fermentation) | 45 min at 22° C. |
| Baking in hearth oven | Putting into the oven at 250° C., baking for 22 min at 230° C. |

(iv) Brioche Obtained from a Frozen Raw Dough

The brioche is obtained from a dough frozen before fermentation.

The recipe is shown in Table 5 and the protocol applied is given in Table 6.

The control yeast (Bruggeman brown) is a baker's yeast used conventionally for this type of breadmaking.

TABLE 5

| Ingredients | Quantity in grams | Quantity as % of the baker |
|---|---|---|
| Flour | 1500 | 100 |
| Water | 525 | 35 |
| Salt | 30 | 2 |
| Yeast | 45 | 3 (2 for the control) |

TABLE 5-continued

| Ingredients | Quantity in grams | Quantity as % of the baker |
|---|---|---|
| Improver (Ibis Violet) | 12 | 0.8 |
| Sugar | 180 | 12 |
| Butter | 375 | 25 |
| Eggs | 375 | 25 |

The improver supplies the mixture of oxidants and reducing agents, the enzymes as well as the conventional emulsifiers for optimizing the production process, good quality and good storage of the breads obtained.

The unsliced brioche is packed in a plastic bag.

TABLE 6

| Kneader | spiral |
|---|---|
| Kneading 1st speed | 5 min |
| Kneading 2nd speed | 5 min |
| Temperature of the dough | 25° C. |
| Initial fermentation (1st fermentation) | 10 min |
| Division | 50 g |
| Deep-freezing | 15 min at −30° C. |
| Thawing | 15 h at 4° C. or 2 h at room temperature |
| Final proving (2nd fermentation) | 90 min |
| Baking | 12 min at 190° C. |

(v) Rotimani

Rotimani is an Indonesian sandwich bread obtained from a dough with a very high sugar content (23 wt % relative to the weight of flour).

The recipe is shown in Table 7 and the protocol applied is given in Table 8.

The control yeast (Bruggeman brown) is a baker's yeast used conventionally for this type of breadmaking.

TABLE 7

| Ingredients | Quantity in grams | Quantity as % of the baker |
|---|---|---|
| Flour | 800 | 100 |
| Water | 360 | 45 |
| Salt | 12 | 1.5 |
| Dry yeast | 27.6 (18.4 for the control) | 3.45 (2.3 for the control) |
| Sugar | 184 | 23 |
| Wilmar Shortening (fat) | 80 | 10 |
| Ibis violet Improver | 2.4 | 0.3 |
| Calcium propionate | 2.4 | 0.3 |
| Milk powder | 24 | 3 |
| Eggs | 80 | 10 |

The improver supplies the mixture of oxidants and reducing agents, the enzymes as well as the conventional emulsifiers for optimizing the production process, good quality and good storage of the breads obtained.

The unsliced rotimani is packed in a plastic bag.

TABLE 8

| Kneader | needle-type |
|---|---|
| Kneading 1st speed | 1 min before addition of the fats, 1 min stop for incorporating the fats, then 1 min |
| Kneading 2nd speed | 5 min 30 s |
| Initial fermentation (1st | 10 min |

TABLE 8-continued

| | |
|---|---|
| fermentation) | |
| Relaxation | 10 min |
| Working | |
| Final proving (2nd fermentation) | 90 min at 35° C. |
| Baking | 21 min at 190° C. |

(vi) Sensory Analysis

The sensory evaluation of bakery products (ii) to (v) is carried out by a panel of experts with 12 to 15 persons.

The experts ascribe a score between 0 and 10 for each descriptor and each bakery product.

The average of the scores is then found. The standard deviation in the scoring is also checked, to ensure consensus among the experts.

The experts are qualified persons who have good sensory acuity and are trained in the use of the methods of sensory evaluation and who are capable of performing all the types of tests reliably. The performance of the experts is checked regularly. Training is carried out for maintaining the level of the panel: one or two sessions of one hour take place per week, in conditions corresponding to the AFNOR standards, for learning to describe and accurately score each descriptor between 0 (weak referent) and 10 (dominant referent) for any bread of the product universes defined at the outset.

The panellists work in individual tasting booths, in a special ventilated room. Specialized software is available for questionnaire creation, data acquisition and statistical analysis of the results.

Results

The breadmaking recipes and protocols selected are characterized by the need to use a large amount of yeast. The yeasts used traditionally in recipes and protocols of this type are responsible for the development of a yeasty note in the bakery products thus obtained.

They are for example the following products:
  brioche-type bread (15.2% of sugar) obtained in a bread machine,
  direct-scheme baguette obtained according to a very short scheme (2h),
  brioche obtained from a frozen raw dough, and
  rotimani, i.e. a sandwich bread obtained from a dough with a very high sugar content (23%).

The bakery products obtained with the yeasts derived from the strains according to the invention (I-4445, I-4446 and I-4447) are compared against those obtained with a control yeast, which is in each case a reference baker's yeast for this type of recipe and protocol.

The only parameter that differs with the bakery products obtained with the control yeast is the nature and amount of yeast used: the amount of yeast tested is in fact adjusted so as to reach a fermentative power equivalent to the control yeast and allow bakery products to be obtained that are similar to those obtained with the control yeast, notably in terms of specific volume.

The difference between the specific volume of the bakery products tested and that of the control bakery product is always less than or equal to ±9%.

The bakery products obtained are then evaluated by an expert panel consisting of 12 to 15 persons, who evaluate each bakery product by ascribing a score (from 0 to 10) relating to the descriptors on a reference list. The average of the scores is shown in Tables 9 and 10.

The results regarding the yeasty note are summarized in Table 9.

Despite a larger dose of yeast being used than for the control yeast, the yeasts derived from the strains according to the invention make it possible to reduce the yeasty note of the bakery products, namely to reduce the "yeast" odor and the "yeast" aroma in the various recipes and protocols tested.

TABLE 9

| Original strain of the yeast tested | Brioche-type bread in bread machine | | Baguette in direct scheme | | Brioche obtained from a frozen raw dough | | Rotimani | |
|---|---|---|---|---|---|---|---|---|
| | O | A | O | A | O | A | O | A |
| I-4445 | 2.25 | 1.77 | 3.58 | 2.75 | 2.75 | 2.05 | 2.15 | * |
| I-4446 | 2.17 | 2.38 | 3.58 | 2.86 | 1.56 | 2.13 | 2.40 | * |
| I-4447 | 1.67 | 1.77 | 3.29 | 1.43 | 2.09 | 2.11 | 2.94 | * |
| Control | 3.71 | 2.66 | 5.72 | 3.06 | 2.53 | 2.30 | 3.34 | * |

O: yeast odor/fermented
A: yeast aroma/fermented
*The yeast aroma is not tested for rotimani, as the sugar present in high concentration masks the yeast aroma Moreover, positive notes are emitted from the bakery products obtained with the yeasts according to the invention, at an intensity readily perceptible for the experts (cf. in Table 10).

TABLE 10

| | Original yeast I-4445 | Original yeast I-4446 | Original yeast I-4447 | Control yeast |
|---|---|---|---|---|
| Brioche-type bread in bread machine | | | | |
| almond odor | 3.56 | 2.42 | 2.79 | 1.18 |
| almond aroma | 2.18 | 1.99 | 3.13 | 0.83 |
| rum odor | 1.35 | 2.58 | 1.55 | 1.77 |
| rum aroma | 0.65 | 2.10 | 1.83 | 0.69 |
| Baguette in direct scheme | | | | |
| ripe wheat odor | 4.29 | 1.43 | 4.29 | 1.43 |
| ripe wheat aroma | 4.29 | 1.43 | 4.29 | 1.43 |
| Brioche obtained from a frozen raw dough | | | | |
| rum odor | 1.96 | 1.94 | 1.10 | 1.02 |
| rum aroma | 1.10 | 1.59 | 0.68 | 0.46 |
| Rotimani | | | | |
| rum aroma | 1.35 | 1.70 | 1.38 | 0.49 |
| sweet flavor | 6.27 | 6.04 | 6.63 | 5.69 |

The positive notes are summarized by yeast and type of recipe/protocol in Table 11.

TABLE 11

| Original strain of the yeast tested | Brioche-type bread in bread machine | Baguette in direct scheme | Brioche obtained from a frozen raw dough | Rotimani |
|---|---|---|---|---|
| I-4445 | almond odor and aroma | ripe wheat odor and aroma | rum odor and aroma | rum aroma sugary flavor |
| I-4446 | rum odor and aroma | | odor and aroma rum | rum aroma sugary flavor |
| I-4447 | almond odor and aroma | ripe wheat odor and aroma | | rum aroma sugary flavor |

The positive notes differ depending on the recipe and protocol used.

Thus, the yeasts derived from strain I-4445 and strain I-4447 are very interesting for the manufacture of bakery products in sugar-free dough and with a short scheme, for example for making baguettes in the direct scheme.

The yeasts derived from strain I-4445 and strain I-4446 are very interesting for the manufacture of a bakery product with sweet dough and/or frozen raw dough, for example for making a brioche obtained from a frozen raw dough.

The yeasts derived from strain I-4445, strain I-4446 and strain I-4447 are very interesting for the manufacture of bakery products with sweet dough and/or according to a bread machine protocol, for example for making a brioche-type bread obtained in a bread machine.

The invention will be further described by the following numbered paragraphs:

1. A method of selecting a yeast strain giving a yeast that completely or partially masks yeasty notes, comprising the steps of:
   culturing a yeast strain to be tested to obtain a yeast to be tested,
   preparing a control bakery product starting from a dough comprising flour, salt, water and at least 0.9% of a baker's yeast, wherein the percentage is expressed as weight of dry matter relative to the weight of flour,
   preparing a bakery product to be tested similarly to the control bakery product, except that the yeast used is the yeast to be tested in an amount to obtain a specific volume equivalent to that of the control bakery product,
   selecting at least one yeast that partially or completely masks yeasty notes in the bakery product to be tested in comparison to the control bakery product, and
   selecting the yeast strain corresponding to the yeast that partially or completely masks yeasty notes in the bakery product to be tested.

2. The method according to paragraph 1, wherein the yeast that completely or partially masks yeasty notes has, in a dry form, a fermentative power below 70 ml in a sugar-free dough.

3. The method according to paragraph 1, wherein the yeast that completely or partially masks yeasty notes is obtained by culture of a yeast strain resulting from the method of selection.

4. A composition yielding a bakery product, said composition comprising flour, salt, and at least 0.9% of a yeast that completely or partially masks yeasty notes, wherein the percentage is expressed as weight of dry matter relative to the weight of flour, and wherein said yeast has, in a dry form, a fermentative power below 70 ml in a sugar-free dough.

5. The composition according to paragraph 4, wherein said yeast is obtained by culture of a yeast strain obtained by the method according to paragraph 1 or a strain derived from said yeast strain.

6. The composition according to paragraph 5, wherein said yeast is obtained by culturing the yeast strain deposited at the CNCM under Accession Number I-4445 on Feb. 9, 2011, the yeast strain deposited at the CNCM under Accession Number I-4446 on Feb. 9, 2011, the yeast strain deposited at the CNCM under Accession Number I-4447 on Feb. 9, 2011, or a strain derived from any one of said yeast strains.

7. The composition according to paragraph 4, comprising less than 90% of water, wherein the percentage is expressed as weight relative to the weight of flour.

8. The composition according to paragraph 4, wherein said composition is in dry form.

9. The composition according to paragraph 4, wherein said composition is in the form of an unfermented dough, a fermented dough, a frozen raw dough, a frozen fermented dough, a precooked dough or a frozen precooked dough.

10. The composition according to paragraph 4, further comprising at least 5% of sugar, wherein the percentage is expressed as weight relative to the weight of flour.

11. A method for preparing a composition yielding a bakery as defined in paragraph 4, said method comprising a step of mixing ingredients comprising flour, salt, and at least 0.9% of a yeast that partially or completely masks yeasty notes, wherein the percentage is expressed as weight of dry matter relative to the weight of flour, and wherein said yeast has, in a dry form, a fermentative power below 70 ml in a sugar-free dough.

12. A method for preparing a bakery product comprising steps of:
   a) mixing ingredients comprising flour, salt, water and at least 0.9% of a yeast that completely or partially masks yeasty notes to obtained a dough, wherein the percentage is expressed as weight of dry matter relative to the weight of flour, and wherein said yeast has, in a dry form, a fermentative power below 70 ml in a sugar-free dough,
   b) fermenting the dough to obtain a fermented dough, and
   c) baking the fermented dough to obtain a bakery product.

13. The method according to paragraph 12, wherein the yeast is obtained by culturing a yeast strain selected using the method according to paragraph 1 or a strain derived from said yeast strain.

14. The method according to paragraph 13, wherein the yeast is obtained by culturing the yeast strain deposited at the CNCM under Accession Number I-4445 on Feb. 9, 2011, the yeast strain deposited at the CNCM under Accession Number I-4446 on Feb. 9, 2011, the yeast strain deposited at the CNCM under Accession Number I-4447 on Feb. 9, 2011, or a strain derived from any one of said yeast strains.

15. The method according to paragraph 12, wherein the ingredients in mixing step a) further comprise at least 5% of sugar, wherein the percentage is expressed as weight relative to the weight of flour.

16. The method according to paragraph 12, further comprising a step of deep-freezing the dough obtained in step a), before step b).

It is to be understood that the invention is not limited to the particular embodiments of the invention described above, as variations of the particular embodiments may be made and still fall within the scope of the appended claims.

The invention claimed is:

1. A composition yielding a bakery product, said composition comprising flour, salt, and at least 0.9% of a yeast, wherein the percentage is expressed as weight of dry matter relative to the weight of flour, and wherein said yeast is obtained by culturing the yeast strain under Accession Number I-4445 (CNCM), the yeast strain under I-4446 (CNCM), or the yeast strain under Accession Number I-4447 (CNCM).

2. The composition according to claim 1, comprising less than 90% of water, wherein the percentage is expressed as weight relative to the weight of flour.

3. The composition according to claim 1, wherein said composition is in dry form.

4. The composition according to claim 1, wherein said composition is in the form of an unfermented dough, a fermented dough, a frozen raw dough, a frozen fermented dough, a precooked dough or a frozen precooked dough.

5. The composition according to claim 1, further comprising at least 5% of sugar, wherein the percentage is expressed as weight relative to the weight of flour.

6. A method for preparing a composition yielding a bakery product as defined in claim 1, said method comprising a step of mixing ingredients comprising flour, salt, and at least 0.9% of a yeast, wherein the percentage is expressed as weight of dry matter relative to the weight of flour, and wherein said yeast is obtained by culturing the yeast strain deposited under Accession Number I-4445 (CNCM), the yeast strain deposited under Accession Number I-4446 (CNCM), or the yeast strain deposited under Accession Number I-4447 (CNCM).

7. A method for preparing a bakery product comprising steps of:
  a) mixing ingredients comprising flour, salt, water and at least 0.9% of a yeast to obtain a dough, wherein the percentage is expressed as weight of dry matter relative to the weight of flour, and wherein said yeast is obtained by culturing the yeast strain deposited under Accession Number I-4445 (CNCM), the yeast strain deposited under Accession Number I-4446 (CNCM), or the yeast strain deposited under Accession Number I-4447 (CNCM),
  b) fermenting the dough to obtain a fermented dough, and
  c) baking the fermented dough to obtain a bakery product.

8. The method according to claim 7, wherein the ingredients in mixing step a) further comprise at least 5% of sugar, wherein the percentage is expressed as weight relative to the weight of flour.

9. The method according to claim 7, further comprising a step of deep-freezing the dough obtained in step a), before step b).

* * * * *